United States Patent
Rigler et al.

(10) Patent No.: US 7,259,847 B2
(45) Date of Patent: Aug. 21, 2007

(54) USE OF OPTICAL DIFFRACTION ELEMENTS IN DETECTION METHODS

(75) Inventors: Rudolf Rigler, St-Sulpice (CH); Hans Blom, Kista (SE); Mathias Johansson, Boras (SE); Hard Sverkers, Gothenburg (SE)

(73) Assignee: Gnothis Holding SA, Ecublens (CH)

( * ) Notice: Subject to any disclaimer, the term of this patent is extended or adjusted under 35 U.S.C. 154(b) by 318 days.

(21) Appl. No.: 10/479,177

(22) PCT Filed: May 28, 2002

(86) PCT No.: PCT/EP02/05866

§ 371 (c)(1),
(2), (4) Date: Dec. 1, 2003

(87) PCT Pub. No.: WO02/097406

PCT Pub. Date: Dec. 5, 2002

(65) Prior Publication Data

US 2004/0126780 A1    Jul. 1, 2004

(30) Foreign Application Priority Data

May 29, 2001 (DE) .................. 101 26 083

(51) Int. Cl.
  G01N 21/64   (2006.01)
  G01J 3/30    (2006.01)
(52) U.S. Cl. ............. 356/318; 435/6; 435/288.7; 250/458.1; 436/172
(58) Field of Classification Search ......... 250/458.1, 250/459.1, 461.1, 461.2; 356/317, 318, 417
See application file for complete search history.

(56) References Cited

U.S. PATENT DOCUMENTS

| 5,935,507 | A | 8/1999 | Morito et al. |
| 6,055,106 | A | 4/2000 | Grier et al. |
| 6,434,345 | B2 * | 8/2002 | Watanabe ............ 399/45 |
| 6,455,861 | B1 * | 9/2002 | Hoyt ............ 250/458.1 |
| 2001/0033374 | A1 * | 10/2001 | Hoyt ............ 356/317 |

FOREIGN PATENT DOCUMENTS

| DE | 19748211 | 5/1999 |
| JP | 08131820 | 5/1995 |
| WO | WO 00/58715 | * 10/2000 |

OTHER PUBLICATIONS

Patent Abstracts of Japan vol. 1996, No. 09, Sep. 30, 1996 & JP 08 131820 A (Moritetsukusu:kk), May 28, 1996 abstract.
Johansson M et al: "Design, fabrication, and evaluation of a multichannel diffractive optic rotary joint" Applied optics, optical society if America, Washington, US, vol. 38, No. 8, Mar. 10, 1999, pp. 1302-1310, XP000823450.

* cited by examiner

*Primary Examiner*—F. L. Evans
(74) *Attorney, Agent, or Firm*—Millen, White, Zelano, Branigan, P.C.

(57) ABSTRACT

The invention relates to a method for determining luminescent molecules by means of optical excitation in confocal measurement volumes using a diffractive optical element. The method is particularly suitable for single-molecule determination, e.g. by means of fluorescence correlation spectroscopy or by means of dynamic light scattering. An apparatus suitable for carrying out the method according to the invention is furthermore disclosed.

38 Claims, 5 Drawing Sheets

USE OF OPTICAL DIFFRACTION ELEMENTS IN DETECTION METHODS

DESCRIPTION

The invention relates to a method for determining luminescent molecules by means of optical excitation in confocal measurement volumes using a diffractive optical element. The method is particularly suitable for single-molecule determination, e.g. by means of fluorescence correlation spectroscopy or by means of dynamic light scattering. An apparatus suitable for carrying out the method according to the invention is furthermore disclosed.

The use of fluorescence correlation spectroscopy (FCS) for the detection of analytes is known. EP-B-0 679 251 discloses methods and apparatuses for the detection of analytes by means of fluorescence spectroscopy, the determination being carried out in a convocal measurement volume which is part of the sample to be examined. However, parallel determination in a multiplicity of measurement volumes is possible only to a limited extent and with high technical outlay.

One object on which the present application is based was to provide methods and apparatuses for determining luminescent molecules, in particular by means of fluorescence correlation spectroscopy, which permits parallel determination in multiple confocal volume elements in a simple manner.

Consequently, the invention relates to a method for determining luminescent molecules by means of optical excitation in confocal measurement volumes comprising the steps of:
(a) providing a sample comprising luminescent molecules,
(b) irradiating the sample with an optical excitation device comprising a light source, a diffractive optical element for splitting light passing through into multiple foci and a focusing optical arrangement for focusing multiple light beams passing through into multiple confocal volume elements, and
(c) capturing emission radiation from the multiple confocal volume elements.

Surprisingly, it has been found that splitting excitation light radiated into the sample by means of diffractive optical elements permits the production of multiple confocal volume elements whilst maintaining a light intensity that is sufficient for detection purposes. This principle can be used for the production of multiple confocal point foci for the detection of individual molecules or a small number, e.g. up to 100 molecules in confocal volume elements with the aid of suitable excitation or detection methods.

New microstructure fabrication technologies make it possible to fabricate optical elements with a previously calculated three-dimensional structure which represents a predetermined diffraction grating for a light source. In this case, a desired point pattern generated by light diffraction is converted by means of Fourier transformation into a three-dimensional diffractive structure which is subsequently produced from a suitable material, for example by means of photolithographic etching.

Diffractive optical elements that may be used are, by way of example, three-dimensional optical gratings which, if appropriate, are applied to an optically transparent carrier, and which diffract light passing through and generate a predetermined diffraction pattern, i.e. a desired arrangement of multiple optical foci, in the object plane by means of constructive and destructive interference. An essential advantage when using such diffractive optical elements is that arbitrary arrangements of the foci can be chosen by virtue of the form of the optical grating. In this case, the multiple optical foci are preferably formed by $1^{st}$-order interferences, only minor light losses occurring as a result of 0th- or higher-order interferences.

The production of suitable diffractive optical elements is described, for example in the Dissertation by F. Nikolaef at the Chalmers Institute of Technologies (1999), in the Dissertation by M. Johansson at the Chalmers Institute of Technologies (2001) and in the publication Johansson and Hard (Applied Optics 38(1999), 1302-1310). Suitable materials for producing the optical elements are plastics, glass and composites or other materials having optical transparency for a given wavelength which can be processed by means of photolithographic etching.

A preferred embodiment of the method according to the invention relates to the detection of luminescent molecules in the confocal measurement volumes by means of fluorescence correlation spectroscopy. The method may be carried out in principle according to the method described in EP-B-0 679 251. In this case, the measurement of one or a few analyte molecules is preferably effected in a measurement volume, the concentration of the analyte molecules to be determined preferably being $\leq 10^{-6}$ mol/l and the measurement volume preferably being $\leq 10^{-14}$ l. Substance-specific parameters are determined, which are determined by means of luminescent measurement at the analyte molecules. These parameters may be translation diffusion coefficients, rotation diffusion coefficients or/and the excitation wavelength, the emission wavelength or/and the lifetime of an excited state of a luminescent molecule or the combination of one or more of these measurement quantities. For specifics about equipment details, reference is made to the disclosure of EP 0 679 251.

A preferred feature of the method according to the invention is that the distance between the measurement volume in the sample liquid and the focusing optical arrangement of the light source is $\geq 1$ mm, preferably 1.5 to 10 mm and particularly preferably 2 to 5 mm. It is furthermore preferred for a gas phase region, which may contain air, protective gas or vacuum, to be arranged between the carrier containing the sample liquid and the optical focusing device. Methods and apparatuses for carrying out FCS with a large distance between focusing optical arrangement and confocal measurement volume are described in DE 101 11 420.6.

The method according to the invention is suitable in principle for carrying out any desired determination methods. A preferred embodiment relates to the determination of an analyte in a sample, e.g. for diagnostic applications or for screening for the purpose of identifying active substances which interact with a target substance. For this purpose, one or more analyte-binding substances which carry a marking group, in particular fluorescence marking group, that can be detected by luminescence measurement are added to the sample. In this case, the method according to the invention preferably comprises a determination of the binding of the marking substance to the analyte to be detected. This detection may be effected for example by means of a mobility change of the marking group on account of the binding to the analyte or by means of a change in the luminescence of the marking group (intensity or/and decay time) on account of the binding to the analyte, or by means of so-called cross-correlation if a plurality of marking groups are used.

The cross-correlation determination uses at least two different markings, in particular fluorescence markings, whose correlated signal within the measurement volume is determined. This cross-correlation determination is described for example in Schwille et al. (Biophys. J. 72 (1997), 1878-1886) and Rigler et al. (J. Biotechnol. 63 (1998), 97-109).

The method according to the invention is suitable in particular for the detection of biomolecules e.g. nucleic acids, proteins or other analyte molecules which occur in living organisms, in particular in mammals such as humans. Furthermore, it is also possible to detect analytes which have been produced from biological samples in vitro, e.g. cDNA molecules which have been produced from mRNA by reverse transcription, or proteins which have been produced from mRNA or DNA by in vitro translation. The method is furthermore suitable for the detection of analytes which are present as elements of a library and are intended to exhibit predetermined characteristics, e.g. binding to the detection reagent. Examples of such libraries are phage libraries or ribosomale libraries.

In a particularly preferred embodiment, the determination comprises a nucleic acid hybridization, one or more luminescence-marked probes binding to a target nucleic acid as analyte. Such hybridization methods may be used for example for the analysis of gene expression, e.g. in order to determine a gene expression profile, or for the analysis of mutations, e.g. single-nucleotide polymorphisms (SNP). The method according to the invention is also suitable, however, for determining enzymatic reactions or/and for determining nucleic acid amplifications, in particular in a thermocycling process. Preferred methods for determining nucleic acid polymorphisms are described in DE 100 56 226.4 and DE 100 65 631.5. A two-color or multicolor cross-correlation determination is particularly preferably carried out in this case.

In a further particularly preferred embodiment, the determination comprises the detection of a protein-protein or protein-ligand interaction, in which case e.g. low-molecular-weight active substances, peptides, nucleic acids, etc. may be used as protein ligands. A two-color or multicolor correlation measurement is preferably carried out for such determinations as well.

In an alternative preferred embodiment, so-called "molecular beacon" probes or primers may be used, which—if they are present in the free form—give rise to a different measurement signal in respect of the luminescence intensity or/and decay time than in the bound state.

A further preferred embodiment of the invention comprises a method for the selection of particles in a substance library, a particle having a predetermined property being selected from a population, comprising a multiplicity of different particles. For this purpose, preferably, a population of different particles is provided, particles having a predetermined property are marked, the particles are conducted in a microchannel through a detection element, comprising multiple confocal volume elements, in order to distinguish between marked and unmarked particles and marked particles are removed. The steps of conduction and removal are preferably repeated at least once, the concentration of the particles being reduced preferably by at least the factor 10⁴ in a subsequent cycle compared with a preceding cycle. The particles may be selected for example from cells, parts of cell surfaces, cell organells, viruses, nucleic acids, proteins and low-molecular-weight substances. The method is also suitable for the selection of particles from the combinatorial library which may contain genetic packages such as phages, cells, spores or ribosomes. The particle population preferably contains more than $10^6$ and particularly preferably more than $10^{10}$ different particles. The particles are preferably marked with a luminescence marking group.

Yet another embodiment comprises carrying out a sequence analysis of polymers, in particular biopolymers, luminescent fragments of an analyte present in the sample being determined. This embodiment is suitable in particular for carrying out a nucleic acid sequencing. For this purpose, a carrier particle with a nucleic acid molecule immobilized thereon is preferably provided, essentially all the nucleotide components of at least one base type in at least one strand of the nucleic acid molecule bearing a fluorescence marking. The carrier particle is introduced into a sequencing apparatus comprising a microchannel and retained there, e.g. by means of an IR capture laser, and individual nucleotide components are progressively cleaved from the immobilized nucleic acid molecule, e.g. by treatment with an exonuclease. The cleaved nucleotide components are then conducted through a microchannel, preferably by means of a hydrodynamic flow, and the base sequence of the nucleic acid molecule is determined there in confocal volume elements on the basis of the sequence of cleaved nucleotide components.

The method according to the invention enables a light beam originating from a light source, e.g. a laser, to be split into a plurality of optical foci. The light beam is preferably split into 2-32, in particular into 4-16, optical foci. By using a suitable focusing optical arrangement, confocal volume elements are imaged in the sample from said optical foci. The confocal volume elements expediently have a size of $10^{-18}$ to $10^{-9}$ l, preferably of $10^{-18}$ to $10^{-12}$ l and particularly preferably of $10^{-16}$ to $10^{-14}$ l.

In order to capture radiation, in particular emission radiation from the multiple confocal volume elements, use is preferably made in each case of a separate detector per volume unit or a spatially resolving detection matrix, e.g. an avalanche photodiode matrix or an electronic detector matrix, e.g. a CCD camera.

Splitting the light beam into a plurality of optical foci permits parallel determination in separate confocal volume elements. In a preferred embodiment, these confocal volume elements are provided in respective separate containers of a carrier, preferably of a microstructure.

The volume of these containers is preferably in the range of $\leq 10^{-6}$ l and particularly preferably $\leq 10^{-8}$ l to $10^{-12}$ l. Thus, the carrier may comprise a microwave structure with a plurality of depressions for receiving sample liquid, which for example have a diameter of between 10 and 1000 μm. Suitable microstructures are described e.g. in DE 100 23 421.6 and DE 100 65 632.3. These microstructures may be used for example for determining a nucleic acid hybridization in solution. The carrier furthermore preferably comprises at least one temperature control element, e.g. a Peltier element, which enables temperature regulation of the carrier or/and individual sample containers therein.

The carrier used for the method is expediently configured in such a way that it enables optical detection of the sample. A carrier which is optically transparent at least in the region of the sample containers is therefore preferably used. The carrier may in this case either be fully optically transparent or contain an optically transparent base and an optically opaque covering layer with cutouts in the sample containers. Suitable materials for carriers are, for example, composite carriers made of metals (e.g. silicon for the covering layer) and glass (for the base). Carriers of this type may be produced for example by applying a metal layer with predetermined cutouts for the sample containers onto the glass. Plastic carriers, e.g. made of polystyrene or polymers based on acrylate or methacrylate, may alternatively be used. It is furthermore preferred for the carrier to have a cover for the sample containers, in order to provide a system which is closed and essentially isolated from the surroundings during the measurement.

In a particularly preferred embodiment, a carrier is used which contains a lens element arranged in the beam path between measurement volume and light source or detector of the optical apparatus. By way of example, the lens element may be fitted at the bottom of a microwave structure. A lens element of the type may, for example, be produced by heating and shaping a photoresist using a master mold, e.g. made of metal such as silicon, and then applied onto the carrier. As an alternative—e.g. when using carriers made of a fully plastic structure—the lens elements may be integrated into the carrier, e.g. produced during production by injection molding. The numerical aperture of the optical measuring arrangement may be increased by using a lens element, preferably a convex lens element. This numerical aperture is preferably in the range of 0.5 to 1.2.

The carrier is furthermore preferably coated with a transparent antireflection coating in order to produce a higher refractive index. By way of example, transparent oxides or nitrides may be used as antireflection coatings. Antireflection coatings are preferably also used on the optical arrangement.

Furthermore, electric fields may be generated in the carrier, in particular in the region of the sample containers, in order to achieve concentration of the analytes to be determined in the measurement volume. Examples of electrodes which are suitable for generating such electric fields are described e.g. in DE 101 03 304.4.

The molecule to be determined may be bound to a carrier particle—in particular in the case of a determination in the microwave format or in the case of single molecule sequencing. The carrier particle has a size which enables movement in microchannels and retention at a desired position within a sequenzing apparatus. The particle size is preferably in the range of 0.5-10 μm and particularly preferably 1-3 μm. Examples of suitable materials of carrier particles are plastics such as polystyrene, glass, quartz, metals or semimetals such as silicon, metal oxides such as silicon dioxide or composite materials which contain a plurality of the above-mentioned components. Particular preference is given to using optically transparent carrier particles, for example made of plastics, or particles having a plastic core and a silicon dioxide shell.

Nucleic acid molecules are preferably immobilized on the carrier particle via their 5' end, e.g. by means of covalent or noncovalent interaction. Polynucleotides are particular preferably bound to the carrier by high-affinity interactions between the partners of a specific binding pair, e.g. biotin/streptavidin or avidin, etc. As an alternative, nucleic acid molecules may also be bound to the carrier by means of adsorption or covalently.

Carrier particles to which only a single nucleic acid molecule is bound are preferably used. Carrier particles of this type may be produced by the nucleic acid molecules provided for the determination being brought into contact with the carrier particles in a molar ratio of preferably 1:5 to 1:20, e.g. 1:10, under conditions under which the nucleic acid molecules are immobilized on the carrier.

The carrier-bound nucleic acid molecules, e.g. DNA molecules or RNA molecules, may be present in single-stranded form or double-stranded form. The nucleic acid molecules are preferably present in single-stranded form. When used for sequencing, essentially all the nucleotide components, e.g. at least 90%, preferably at least 95%, of all the nucleotide components, of at least one base type carry a fluorescence marking group. It is also possible for essentially all the nucleotide components of at least two base types, for example 2, 3 or 4 base types, to carry a fluorescence marking, each base type expediently containing a different fluorescence marking group. Nucleic acids marked in this way may be produced by enzymatic primer extension on a nucleic acid matrix using a suitable polymerase, e.g. a thermostable DNA polymerase. A precise description of this method is found in DE 100 31 840.1 and DE 100 65 626.9 and also the literature citations specified therein.

The present invention relates still further to an apparatus for detecting luminescent molecules, in particular for carrying out a method as described above, comprising (a) a carrier for receiving a sample which contains luminescent molecules to be determined, (b) an optical excitation device, comprising a light source, a diffractive optical element for splitting light passing through into multiple foci and a focusing optical arrangement for focusing light passing through into multiple confocal volume elements for the excitation of luminescence in the multiple confocal volume elements, and (c) an optical detection device for detecting luminescence from the multiple confocal volume elements.

The carrier is preferably a microstructure with a plurality of containers, preferably at least 10, particularly preferably at least $10^2$ containers, for receiving a sample liquid, in which case the sample liquid in the separate containers may originate from one or more sources. The introduction of the sample liquid to the containers of the carrier may be effected e.g. by means of a piezoelectric liquid delivery apparatus.

The containers of the carrier are configured in such a way that they enable binding of the detection reagent to the analyte in solution. The containers are preferably depressions in the carrier surface, in which case said depressions may in principle have any desired form, for example circular, square, rhomboid, etc. The carrier may even comprise $10^3$ or more separate containers.

As an alternative, the carrier may also contain a microchannel structure with one or more microchannels which are suitable in particular for a single-molecule sequencing method as described in DE 100 31 840.1 and DE 100 65 626.9 or for a particle selection method as described in DE 100 31 028.1.

The optical excitation device comprises a strongly focused light source, preferably a laser beam, which is focused onto the measurement volume in the sample liquid by means of corresponding optical devices. The light source may also contain two or more laser beams, which are then respectively focused onto the measurement volume by different optical arrangements before entering the sample liquid. If two or more laser beams are used, a separate diffractive optical element may be used for each laser beam. The detection device may contain for example a fiber-coupled avalanche photodiode detector or an electronic detector. However, it is also possible to use excitation or/and detection matrices comprising a point matrix of laser points produced by a diffraction optical arrangement or a quantum well laser, as well as a detector matrix produced by an avalanche photodiode matrix or an electronic detector matrix, e.g. a CCD camera.

The carrier may be provided in prefabricated form, a plurality of separate containers of the carrier being filled with luminescence-marked detection reagents, preferably luminescence-marked hybridization probes or primers. The carrier containing the detection reagents is then expediently dried.

In a preferred embodiment of the invention, a prefabricated carrier is provided which contains a multiplicity of separate containers, e.g. 100 containers, which are respectively filled with different detection reagents, e.g. reagents for the detection of a nucleic acid hybridization such as primers or/and probes. This carrier may then be filled with a sample originating from an organism to be examined, e.g. a human patient, so that different analytes from a single sample are determined in the respective containers. Carriers of this type may be used for example to compile a gene expression profile, e.g. for the diagnosis of diseases, or for the determination of nucleic acid polymorphisms, e.g. for the detection of a specific genetic predisposition.

Finally, the invention relates to the use of a diffractive optical element for producing multiple optical foci for parallel determination of molecular interactions in multiple confocal volume elements. Particular preference is attached to the use for fluorescence correlation spectroscopy, as explained in detail above. However, the diffractive optical elements may also be used for other methods, e.g. for dynamic laser light scattering, wherein the intensity fluctuation is determined by means of scattered light in confocal volume elements.

The invention will furthermore be explained by means of the accompanying figures and examples.

Figure 1:
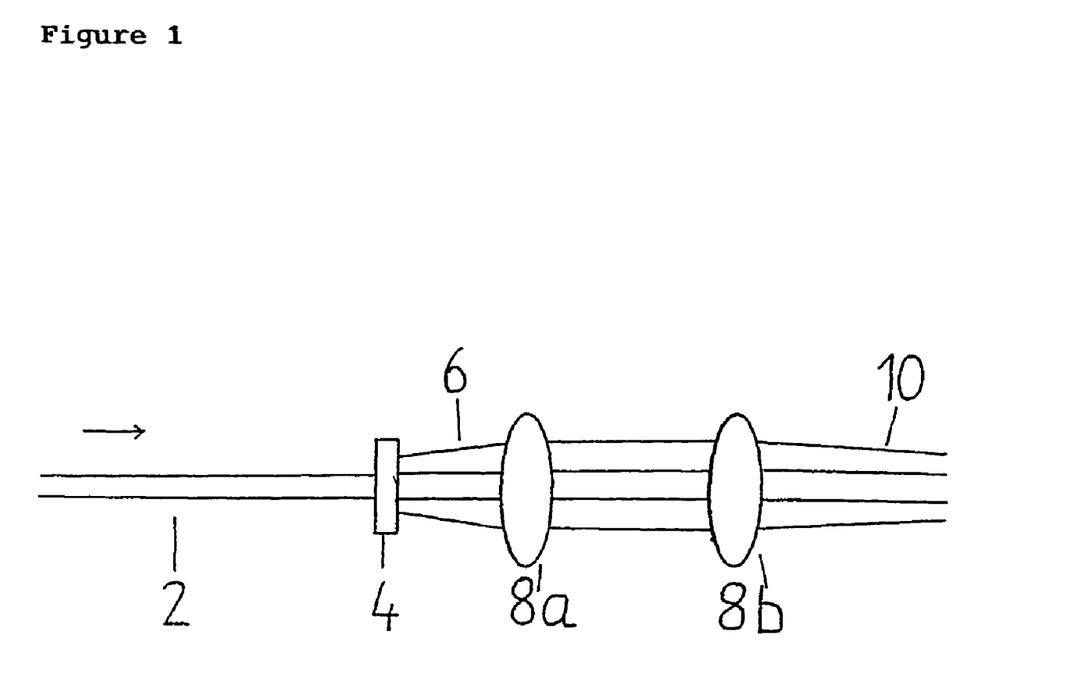

FIG. 1 shows the diagrammatic illustration of an embodiment of the method according to the invention. A light beam (2), e.g. a laser beam, is split into a plurality of partial beams (6), e.g. four partial beams (6), in a diffractive optical element (4) and conducted in an optical focusing device (8a, 8b). The partial beams (10) emerging there are bundled in such a way that they form confocal volume elements with a predetermined size at a predetermined distance from the optical focusing device.

Figure 2:
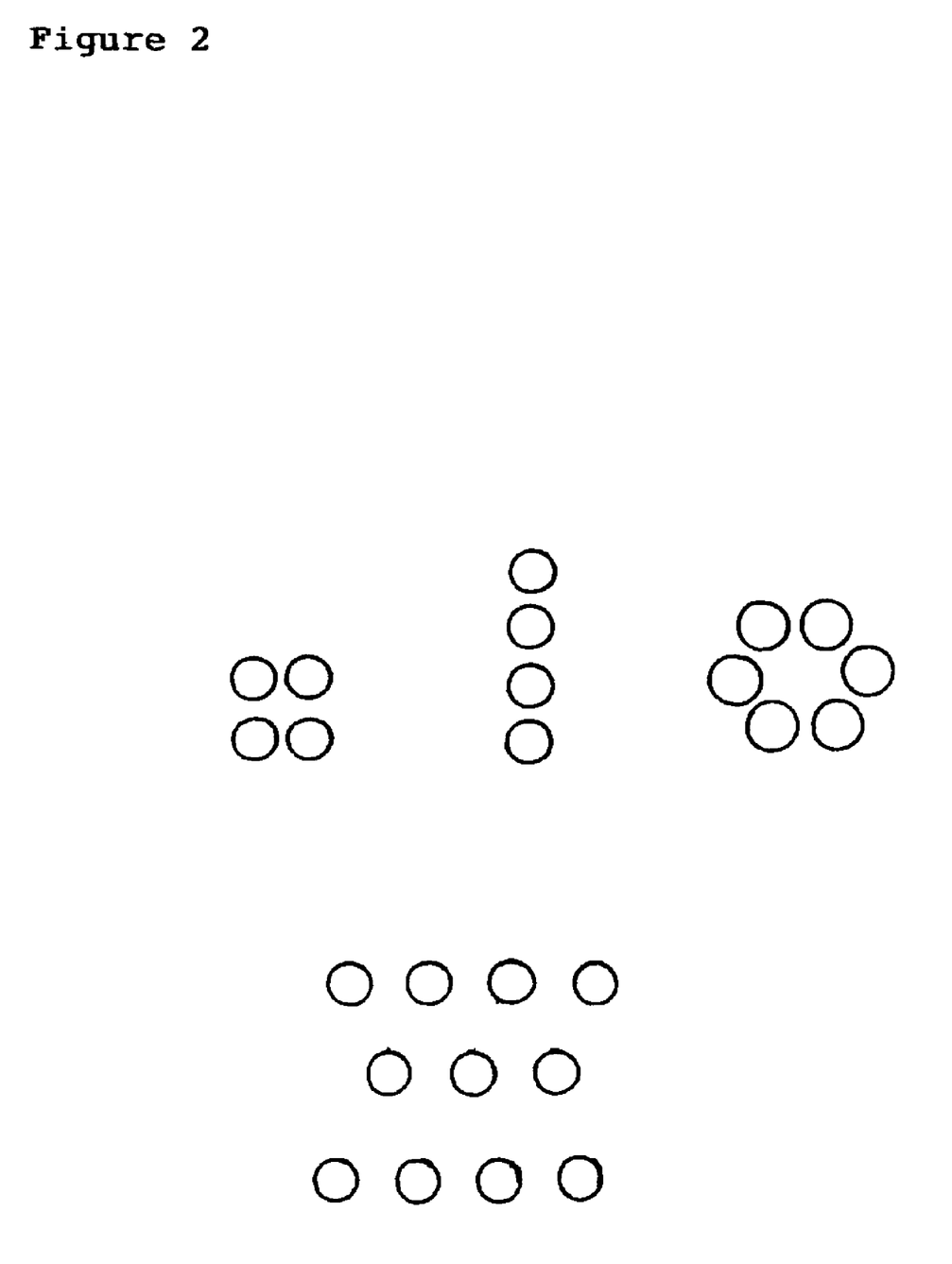

FIG. 2 shows exemplary arrangements for multiple optical foci which can be produced by means of the diffractive optical element. In principle, the arrangement of the foci is freely selectable. The foci are preferably formed from $1^{st}$-order interferences. The losses due to interferences of zeroth order and higher orders are low and preferably amount to $\leq 30\%$.

Figure 3:
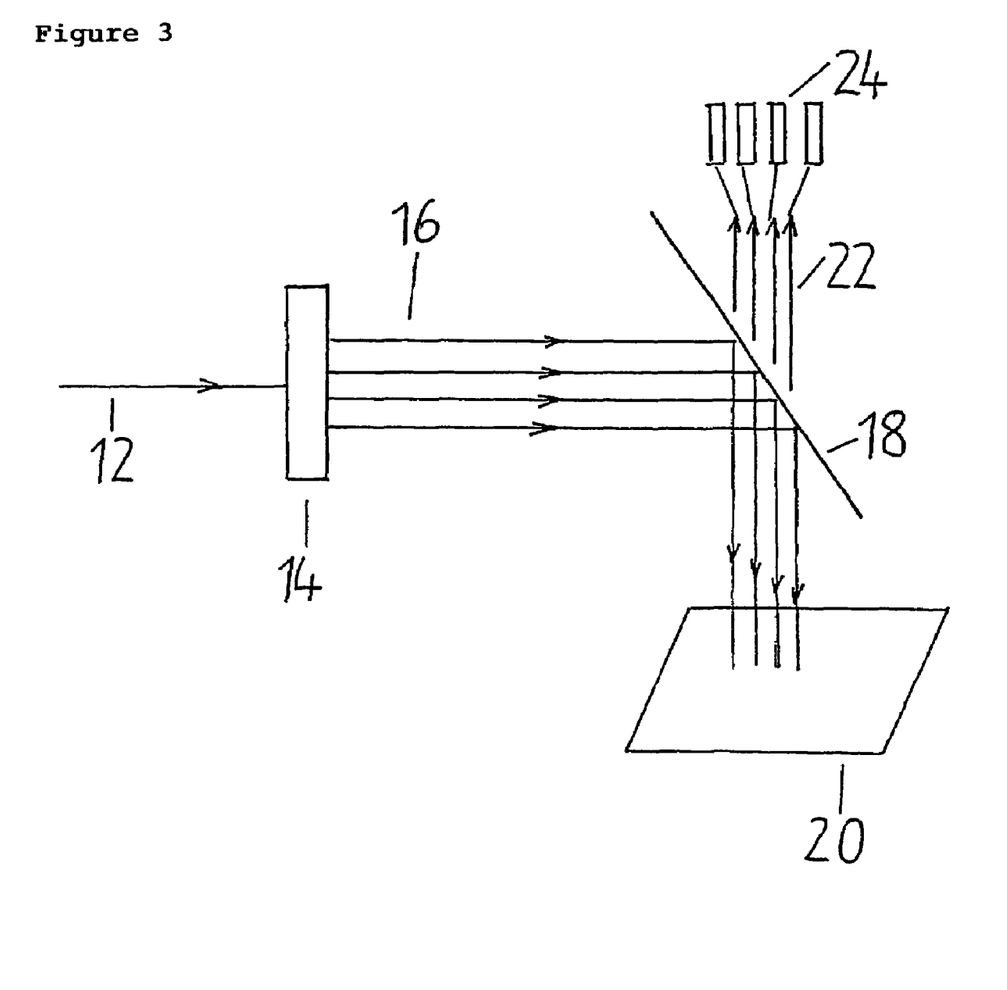

FIG. 3 shows a further embodiment of the method according to the invention. A laser beam (12) is split into a plurality of partial beams (16), e.g. four partial beams (16), by means of a diffractive optical element (14), which partial beams produce a predetermined pattern of optical foci. The partial beams are subsequently deflected by a dichroic mirror (18) and directed via a focusing optical arrangement (not shown) onto a carrier (20), where they form a plurality of confocal volume elements. Light (22) emitted from the confocal volume elements, e.g. by fluorescence, is captured and detected by detectors (24).

Figure 4:
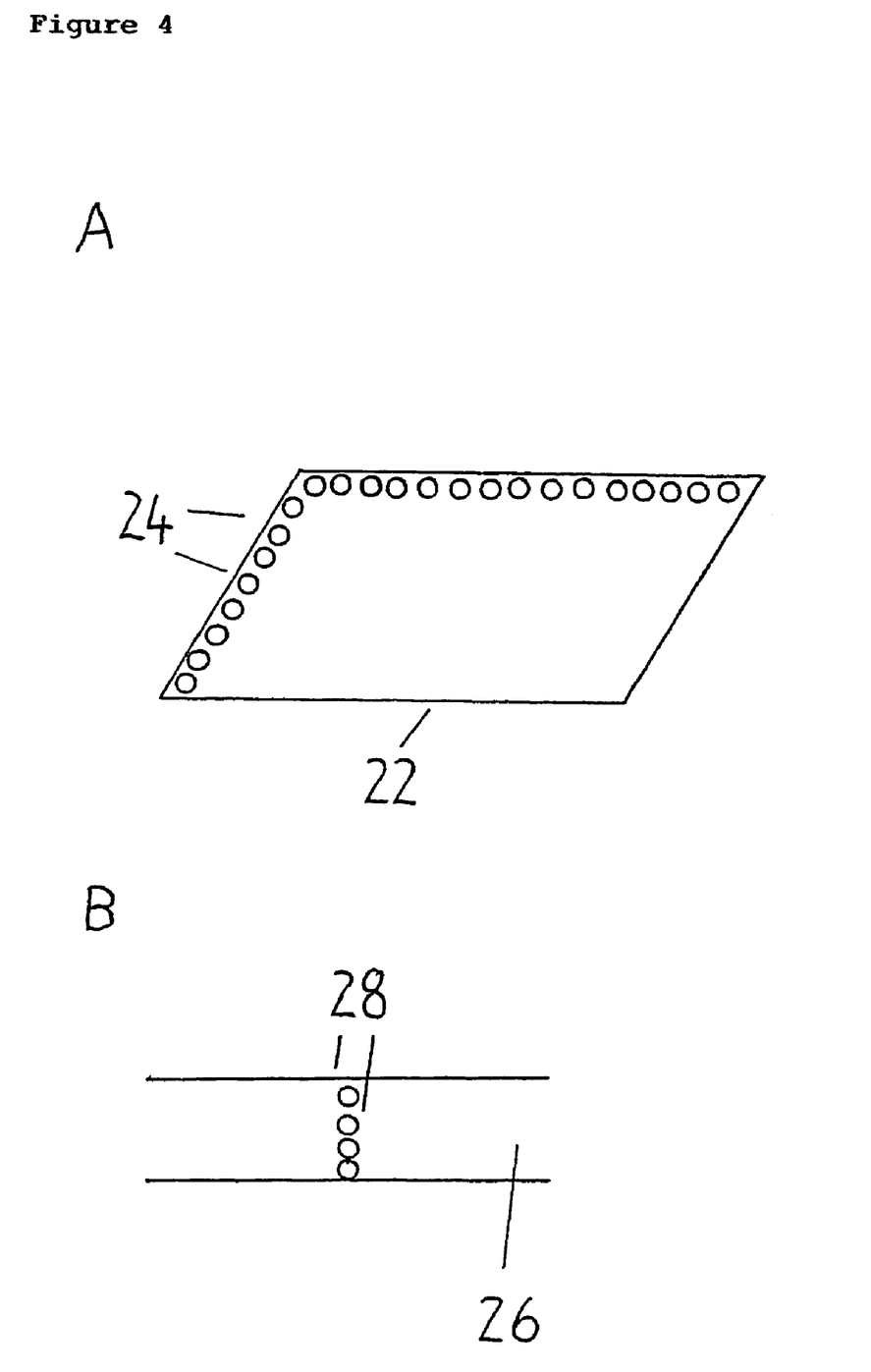

FIGS. 4A and 4B show preferred embodiments for suitable carriers. The carrier in accordance with FIG. 4A is a microstructure, e.g. in the form of a chip, having at least $10^2$ separate sample containers (24). The distance between two sample containers is preferably 50-150 μm, e.g. 100-110 μm. The density of the containers is preferably in the range of 100-10,000 depressions per $cm^2$. The sample volume in the individual containers is preferably $10^{-6}$ to $10^{-12}$ l. A confocal volume element for measuring interactions between individual molecules or a small number of molecules is formed within the sample volume. The carrier shown in FIG. 4A is suitable in particular for high-throughput diagnosis and active substance screening methods. If the number of containers within the carrier is greater than the number of partial beams generated by the diffractive optical element, the carrier can be scanned in a plurality of steps. For this purpose, the optical arrangement or/and the carrier may be readjusted in each case for the individual steps by means of suitable measures.

FIG. 4B shows a microchannel (26) with confocal volume elements (28) arranged therein. This microchannel structure may be used in particular for single-molecule sequencing or for single-molecule selection.

Figure 5:
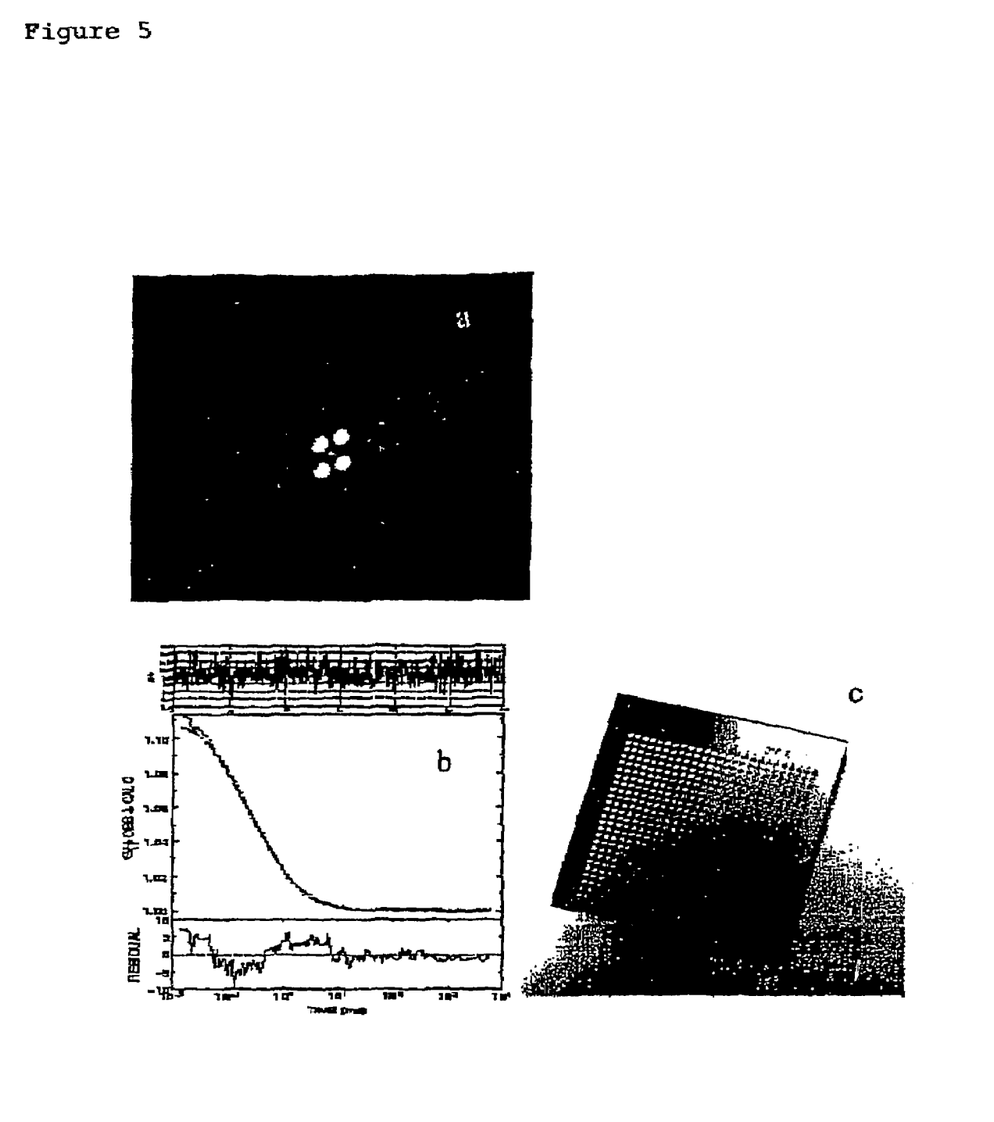

FIG. 5A shows a 2×2 pattern of multiple optical foci (bright spots), produced by a diffractive optical element.

FIG. 5B shows the autocorrelation curve of 10 fluorescence reporter molecules in one of the multiple foci. It was found that the autocorrelation curve is identical in each case in all four foci.

FIG. 5C shows a representation of a biochip microarray having a diameter of 300 μm with 25×25 depressions for receiving samples, which is suitable for carrying out the method according to the invention.

The invention claimed is:

1. A method for determining luminescent molecules by optical excitation in confocal measurement volumes comprising the steps of:
   (a) providing a sample comprising luminescent molecules,
   (b) irradiating the sample with an optical excitation device comprising a light source, a diffractive optical element for splitting light passing through into multiple foci and a focusing optical arrangement for focusing multiple light beams passing through into multiple confocal volume elements of a size of $10^{-18}$ to $10^{-9}$ l, and
   (c) capturing emission radiation from the multiple confocal volume elements.

2. The method as claimed in claim 1, wherein the luminescent molecules are selected from luminescence-marked detection reagents which bind to an analyte present in the sample.

3. The method as claimed in claim 1 wherein the determination comprises a nucleic acid hybridization, one or more luminescence-marked probes binding to a target nucleic acid.

4. The method as claimed in claim 1 wherein the determination comprises an enzymatic reaction.

5. The method as claimed in claim 1 wherein the determination comprises a nucleic acid amplification.

6. The method as claimed in claim 1 wherein the determination comprises a mutation analysis for nucleic acids.

7. The method as claimed in claim 1, wherein the determination comprises gene expression analysis for nucleic acids.

8. The method as claimed in claim 1, wherein the determination comprises a particle selection.

9. The method as claimed in claim 1, wherein the determination comprises a nucleic acid sequencing.

10. The method as claimed in claim 1, wherein a laser is used as light source.

11. The method as claimed in claim 1, wherein the diffractive optical element used is a three-dimensional optical grating which optionally is applied on an optically transparent carrier, which diffracts light passing through and generates a predetermined diffraction pattern, comprising multiple optical foci.

12. The method as claimed in claim 1, wherein the multiple optical foci are formed by $1^{st}$ order interferences.

13. The method as claimed in claim 1, wherein a light beam is split into 2 to 32 optical foci.

14. The method as claimed in claim 1, wherein the confocal volume elements have a size of $10^{-18}$ to $10^{-12}$ l.

15. The method as claimed in claim 1, wherein a separate detector or a spatially resolving detection matrix is in each case used for capturing emission radiation from the multiple confocal volume elements.

16. A method for determining luminescent molecules by optical excitation in confocal measurement volumes comprising the steps of:
   (a) providing a sample comprising luminescent molecules,
   (b) irradiating the sample with an optical excitation device comprising a light source, a diffractive optical element for splitting light passing through into multiple foci and a focusing optical arrangement for focusing multiple light beams passing through into multiple confocal volume elements, and
   (c) capturing emission radiation from the multiple confocal volume elements wherein the distance between the focusing optical arrangement of the light source and a confocal volume element is $\geq 1$ mm.

17. The method as claimed in claim 1, wherein the sample is thermally insulated from the light source and from the focusing optical arrangement.

18. The method as claimed in claim 1, wherein the sample is provided in a carrier with a plurality of separate containers.

19. The method as claimed in claim 1, wherein the optical measurement arrangement has a numerical aperture of 0.5 to 1.2.

20. The method as claimed in claim 1, wherein the carrier contains a plurality of separate containers for receiving samples.

21. A method for determining luminescent molecules by optical excitation in confocal measurement volumes comprising the steps of:
   (a) providing a sample comprising luminescent molecules,
   (b) irradiating the sample with an optical excitation device comprising a light source, a diffractive optical element for splitting light passing through into multiple foci and a focusing optical arrangement for focusing multiple light beams passing through into multiple confocal volume elements, and
   (c) capturing emission radiation from the multiple confocal volume elements wherein the sample is provided in a microchannel structure.

22. The method as claimed in claim 21, wherein an analyte present in the sample is retained in the microchannel structure.

23. The method as claimed in claim 21, wherein an analyte present in the sample is subjected to a separation reaction, fragments separated off from the analyte being determined.

24. The method as claimed in claim 21, wherein the microchannel structure has one or more channels with a diameter of 1-100 mm.

25. The method as claimed in claim 1 wherein an analyte present in the sample is coupled to a carrier particle.

26. The method as claimed in claim 25, wherein a carrier particle made of plastic, glass quartz, metals, semimetals or made of a composite material is used.

27. The method as claimed in claim 25, wherein the carrier particle has a diameter of 0.5-10 μm.

28. An apparatus for determining luminescent molecules, by a method as claimed in claim 1, comprising
   (a) a carrier for receiving a sample which contains luminescent molecules to be determined,
   (b) an optical excitation device, comprising a light source, a diffractive optical element for splitting light passing through into multiple foci and a focusing optical arrangement for focusing light passing through into multiple confocal volume elements of a size of $10^{-18}$ for $10^{-9}$ l for the excitation of luminescence in the multiple confocal volume elements, and
   (c) an optical detection device for detecting luminescence from the multiple confocal volume elements.

29. The apparatus as claimed in claim 28 wherein the carrier comprises a microstructure with at least 10 separate containers for receiving samples.

30. A method for determining molecular interactions among molecules by optical excitation in confocal measurement volumes comprising the steps of:
   (a) providing a sample comprising said molecules,
   (b) irradiating the sample with an optical excitation device comprising a light source, a diffractive optical element for splitting light passing through into multiple foci and a focusing optical arrangement for focusing multiple light beams passing through into multiple confocal volume elements of a size of $10^{-18}$ to $10^{-9}$ l, and
   (c) capturing emission radiation from the multiple confocal volume elements.

31. The method as claimed in claim 30 for fluorescence correlation spectroscopy.

32. The method as claimed in claim 30 for dynamic laser light scattering.

33. The method of claim 16 wherein said distance is 1.5-10 mm.

34. The method of claim 16 wherein said distance is 2-5 mm.

35. A method claim 16 wherein the light beam is split into 4-16 optical foci.

36. A method of claim 18 wherein there are at least $10^2$ speparate containers.

37. A method of claim 20 wherein there are at least $10^2$ speparate containers.

38. A method of claim 5 wherein said amplification comprises a thermocycling process.

* * * * *

UNITED STATES PATENT AND TRADEMARK OFFICE
CERTIFICATE OF CORRECTION

PATENT NO. : 7,259,847 B2
APPLICATION NO. : 10/479177
DATED : August 21, 2007
INVENTOR(S) : Rudolf Rigler Page 1 of 1

It is certified that error appears in the above-identified patent and that said Letters Patent is hereby corrected as shown below:

On the front page, Inventors: item (75) line 3, reads "Hard Sverkers," should read -- Sverker Hard, --
Column 8, line 37, reads "claim 1 wherein" should read -- claim 1, wherein --
Column 8, line 41, reads "claim 1 wherein" should read -- claim 1, wherein --
Column 8, line 43, reads "claim 1 wherein" should read -- claim 1, wherein --
Column 8, line 45, reads "claim 1 wherein" should read -- claim 1, wherein --
Column 8, line 55, reads "used as light" should read -- used as the light --
Column 9, line 39, reads "multiple foci and" should read -- multiple foci, and --
Column 10, line 1, reads "claim 1 wherein" should read -- claim 1, wherein --
Column 10, line 4, reads "glass quartz," should read -- glass, quartz, --
Column 10, line 17, reads "for $10^{-9}$ 1" should read -- to $10^{-9}$ 1 --
Column 10, line 22, reads "claim 28 wherein" should read -- claim 28, wherein --
Column 10, Line 31, reads "multiple foci and" should read --multiple foci, and --
Column 10, line 37, reads "claim 30 for" should read -- claim 30, for --
Column 10, line 39, reads "claim 30 for" should read -- claim 30, for --
Column 10, line 41, reads "claim 16 wherein" should read -- claim 16, wherein --
Column 10, line 43, reads "claim 16 wherein" should read -- claim 16, wherein --
Column 10, line 46, reads "claim 16 wherein" should read -- claim 13, wherein --
Column 10, line 48, reads "claim 18 wherein" should read -- claim 18, wherein --
Column 10, line 49, reads "speparate" should read -- separate --
Column 10, line 50, reads "claim 20 wherein" should read -- claim 20, wherein --
Column 10, line 51, reads "speparate" should read -- separate --
Column 10, line 52, reads "claim 5 wherein" should read -- claim 5, wherein --

Signed and Sealed this

Fifteenth Day of April, 2008

JON W. DUDAS
*Director of the United States Patent and Trademark Office*